United States Patent [19]

Waller

[11] Patent Number: 5,105,047

[45] Date of Patent: Apr. 14, 1992

[54] CATALYSIS USING BLENDS OF PERFLUORINATED ION-EXCHANGE POLYMERS WITH PERFLUORINATED DILUENTS

[75] Inventor: Francis J. Waller, Allentown, Pa.

[73] Assignee: E. I. Du Pont de Nemours and Company, Wilmington, Del.

[21] Appl. No.: 388,402

[22] Filed: Aug. 2, 1989

[51] Int. Cl.$^5$ .............................................. C07C 2/04
[52] U.S. Cl. .................................. 585/515; 502/402;
502/507; 585/458; 585/526; 585/462; 585/730;
585/470
[58] Field of Search ............... 502/108, 402, 507, 155;
585/458, 515, 526, 462

[56] References Cited

U.S. PATENT DOCUMENTS

| | | | |
|---|---|---|---|
| 3,282,875 | 11/1966 | Connelly et al. | 260/29.6 |
| 3,624,053 | 11/1971 | Gibbs et al. | 260/79.3 |
| 3,849,243 | 11/1974 | Grot | 161/189 |
| 4,038,213 | 7/1977 | McClure et al. | 252/430 |
| 4,176,215 | 11/1979 | Molnar et al. | 521/27 |
| 4,303,551 | 12/1981 | Vaughan | 252/430 |
| 4,367,352 | 1/1983 | Watts, Jr. et al. | 585/526 |
| 4,433,082 | 2/1984 | Grot | 524/755 |
| 4,591,439 | 5/1986 | Grot | 210/638 |

FOREIGN PATENT DOCUMENTS

| | | | |
|---|---|---|---|
| 7067525 | 10/1980 | Japan | 585/458 |
| 2090856 | 7/1982 | United Kingdom | 585/458 |

OTHER PUBLICATIONS

Waller et al., *Chemtech*, Jul. 1987, pp. 438–441.
Kapura et al., *Ind. Eng. Chem. Prod. Res. Develop.*, vol. 12, No. 1, pp. 62–66 (1973).

*Primary Examiner*—Asok Pal

[57] ABSTRACT

Improved processes for acid-catalyzed oligomerization of olefins and alkylation of toluene are disclosed using a catalyst blend of at least one perfluorinated ion-exchange polymer containing sulfonic acid groups and at least one polymer diluent in a nonpolar reaction mixture.

21 Claims, No Drawings

CATALYSIS USING BLENDS OF PERFLUORINATED ION-EXCHANGE POLYMERS WITH PERFLUORINATED DILUENTS

FIELD OF THE INVENTION

This invention relates to improved processes for selected acid-catalyzed hydrocarbon conversion reactions.

BACKGROUND OF THE INVENTION

"Hydrocarbon conversion reactions" encompass a broad range of both isomerization and oligomerization reactions, many of which are of vital interest to the chemical and petroleum industries. Increasingly, these reactions provide major sources of such petrochemical commodities as toluene and olefin oligomers. Hence, there is a need for improved processes for the preparation of such compounds.

Many of the hydrocarbon conversion reactions of interest to the chemical and petrochemical industries can be catalyzed by suitable acid catalysts. Heterogeneous acid catalysts are generally preferred in such reactions, due to ease of product separation and catalyst regeneration. One particularly attractive class of heterogeneous acid catalysts is that of the perfluorinated ion-exchange polymers which have a substantially fluorinated aliphatic backbone with pendant sulfonic, carboxylic or phosphonic acid groups. These perfluorinated ion-exchange polymers combine relatively high thermal and chemical stability with very high Hammett acidities. The use of such polymers in various hydrocarbon conversion reactions has been reviewed by Waller et al., Chemtech. July 1987, pp. 438-441 and references therein.

Particularly useful in many acid-catalyzed reactions are the perfluorinated ion-exchange polymers containing sulfonic acid groups due to their high acid activity, thermal stability, ease of separation from reaction mixture, and ease of regeneration. Typical examples of such polymers are those described in U.S. Pat. Nos. 3,282,875; 3,624,053; 3,849,243; 4,038,213; 4,303,551; or 4,661,411. Blends and laminates of perfluorinated polymers having sulfonic acid groups with other polymers are also known.

U.S. Pat. No. 4,176,215 teaches ion-exchange films, membranes and laminar structures incorporating a layer of a blend of a first fluorinated polymer containing sulfonyl groups in ionizable form with a second fluorinated polymer containing carboxylic acid functional groups. Such films and membranes are used in chloralkali electrolysis cells.

U.S. Pat. No. 4,433,082 discloses a process useful in recovering perfluorinated polymers having sulfonic acid or sulfonate groups from scrap and used articles containing such polymers. Example 7 teaches a scrap membrane having one layer of a copolymer of tetrafluoroethylene and perfluoro(3,6-dioxa-4-methyl-7-octenesulfonyl fluoride) in —$SO_3H$ form and one layer of a copolymer of tetrafluoroethylene and methyl perfluoro(4,7-dioxa-5-methyl-8-nonenoate) in —$COOCH_3$ form and a reinforcing fabric of polytetrafluoroethylene.

U.S. Pat. No. 4,591,439 discloses an ion-exchange device with cation exchange membranes of perfluorinated polymers having sulfonyl functional groups. Preferably the polymers are present as copolymers with tetrafluoroethylene or tetrafluoroethylene and hexafluoropropylene.

European Patent Application 291,033 published Nov. 17, 1988, discloses use of perfluorinated acid ion-exchange resins as effective catalysts for the isomerization of 3-pentenoic compounds to 4-pentenoic compounds. Blends of perfluorinated sulfonic acid and perfluorinated carboxylic acid polymers are employed. Preferred are blends of tetrafluoroethylene copolymers with methylperfluoro-5-methyl-4,7-dioxanon-8-eneoate and tetrafluoroethylene copolymers with perfluoro-(3,6-dioxa-4-methyl-7-octene)sulfonic acid, each containing 0.1 to 4% of a noble metal in an oxidation state of at least +2 incorporated into the polymer.

Kapura et al., "Sulfonated Polymers as Alkylation Catalysts", Industrial Engineering Chemistry Product Research Development, Vol. 12, No. 1, pp. 62-66 (1973), disclosed that a sulfonated fluorocarbon vinyl ether polymer was inactive in alkylating isobutane with propylene in the gas phase and in a mole ratio of 5 to 1 at 260° C. The conclusion reached in that study was that the sulfonated fluorocarbon vinyl ether polymer catalyst was too weakly acidic to catalyze paraffin alkylation and that the polymer was not a useful catalyst. That study also showed that these same ion-exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C.".

A major disadvantage of these polymers, however, is their relatively high cost. A need exists, therefore, to develop cheaper and/or more active catalysts which retain the high thermal and chemical stability of the perfluorinated ion-exchange polymers.

This invention provides improved processes for selected hydrocarbon conversion reactions, wherein the improvement is the use of a catalyst which is a blend of a perfluorinated ion-exchange polymer with pendant —$SO_3H$ groups and an inert perfluorinated polymer diluent in a nonpolar reaction mixture This diluted catalyst blend is unexpectedly more active on an acid-equivalent basis, and hence less expensive to use, than the perfluorinated polymer with —$SO_3H$ groups alone.

SUMMARY OF THE INVENTION

This invention provides an improved process for the acid-catalyzed oligomerization of olefins, wherein an olefin selected from the group of monoolefins containing at least two carbon atoms is contacted with an acid catalyst at a temperature of from about 80° C. to about 240° C., wherein the improvement is the use of a catalyst which is a blend of at least one perfluorinated ion-exchange polymer containing sulfonic acid groups and at least one perfluorinated polymer diluent in a substantially nonpolar reaction mixture.

This invention also provides an improved process for the acid-catalyzed alkylation of toluene, wherein toluene is contacted with an olefin chosen from the group of monoolefins containing at least 2 carbon atoms at a temperature of from about 80° C. to about 240° C. in the presence of an acid catalyst, wherein the improvement is the use of a catalyst which is a blend of at least one perfluorinated polymer containing sulfonic acid groups and at least one perfluorinated polymer diluent in a substantially nonpolar reaction mixture.

DETAILED DESCRIPTION OF THE INVENTION

Suitable acid catalysts for the processes of this invention are blends of at least one perfluorinated ion-exchange polymer containing sulfonic acid groups and at least one perfluorinated polymer diluent, where the combined weight ratio of acid polymer to diluent is between 99:1 and 1:1. Suitable perfluorinated polymers containing —SO$_3$H groups are known in the art and include the Nafion ® polymers, available from E. I. du Pont de Nemours and Company. Nafion ® is a substantially perfluorinated ion-exchange polymer which contains pendant sulfonic acid groups which Du Pont sells as catalysts for use in the manufacture of industrial chemicals. However, it is generally preferable to blend the melt-processible precursor of the perfluorinated polymer with the perfluorinated diluent before conversion of the functional groups to their acid forms. Suitable perfluorinated sulfonyl-containing polymers include those described in U.S. Pat. Nos. 4,330,654; 4,329,435; 4,358,545; 4,417,969; and 3,282,875 which are hereby incorporated by reference.

Suitable perfluorinated polymer diluents for use in the catalyst blends are substantially perfluorinated polymers which contain functional groups which are inert under the hydrocarbon conversion reaction conditions. Suitable perfluorinated polymer diluents include, but are not limited to, poly(tetrafluoroethylene) (PTFE), copolymers of tetrafluoroethylene and hexafluoropropylene, perfluorinated ion-exchange polymers containing carboxylic acid functional groups, and copolymers of tetrafluoroethylene and perfluorinated ion-exchange polymers containing carboxylic acid functional groups, or derivatives thereof.

The blends are not limited to two-component blends; multi-component blends are also possible. One example is a blend of two sulfonic acid-containing polymers with one diluent polymer. The two sulfonic acid-containing polymers could be different compositions, or be based on the same monomers but having different equivalent weights. Another example is a blend of one sulfonic acid-containing polymer with two diluent polymers. The two diluent polymers could be two polymers of different compositions or be based on the same monomer but having different equivalent or molecular weights. Preferably, the catalyst is a blend of perfluorinated sulfonic acid polymers and tetrafluoroethylene in the ratio of 20:1 to 1:1, most preferably, from 10:1 to 1:1.

The catalyst blends can be prepared by coextruding the thermoplastic forms of the polymers as known in the art. See for example U.S. Pat. No. 4,176,215. Powders, granules, or pellets of the individual polymers can first be mixed together. Such a mixture is then subjected to heat and pressure by various means, such as pressing, extruding in a screw extruder, or working on a roll mill or rubber mill. To assure formation of an intimate, uniform blend, the steps can be repeated two or more times. For example, pressed films can be flaked or cut into small pieces and repressed into film. Extruded polymer can be chopped into pellets as it is extruded, and then reextruded. Powders for blending can be made by grinding in a mill or cold grinding in a freezer mill.

The sulfonyl groups are then converted to sulfonic acid groups. Such conversion is ordinarily accomplished by hydrolysis carried out with an aqueous solution of a mineral acid or alkali metal hydroxide. Base hydrolysis is preferred. Use of hot solutions, near the boiling point of the solution, is preferred for rapid hydrolysis. It can also be of advantage to include a water-miscible organic compound such as dimethylsulfoxide in the hydrolysis bath.

In one aspect of the present invention, a monoolefin containing at least two carbon atoms, or a mixture of such monoolefins, is contacted with an acid catalyst at a temperature of from about 80° C. to about 240° C., wherein the acid catalyst is a blend of at least one perfluorinated polymer containing sulfonic acid groups and at least one perfluorinated polymer diluent.

Preferred monoolefins are C$_2$ to C$_5$ monoolefins, for example, ethylene, propylene, isobutylene, 1-butene, 2-butene, 2-methyl-2-butene, and mixtures thereof. The monoolefin(s) can also be diluted with an inert gas, such as nitrogen.

The reaction can be carried out either as a batch or continuous type of operation. When employed as a batch operation, the use of vigorous mechanical stirring or shaking is recommended. When employed as a continuous process, the feedstreams can be contacted with the catalyst in any suitable reactor. The pressure in the reaction zone will depend on the reactor configuration, temperature and olefin reactants, but can be between about 0.01 atm. to about 150 atm. Preferably, the pressure is between about 0.1 atm. and about 75 atm. The reaction can be run in the gas phase or the liquid phase, depending on the temperature and pressure.

Reaction temperatures can be varied between about 80° C. and about 240° C. Although the activity of the catalyst generally increases with increasing temperature, the catalyst may begin to decompose above about 250° C. The preferred reaction temperature is between about 150° C. and 200° C.

The reaction products obtained are primarily mixtures of olefin oligomers, but may also contain products derived from the acid-catalyzed rearrangement and/or alkylation of the oligomers.

In another aspect of this invention, toluene is contacted with an olefin chosen from the group of monoolefins containing at least 2 carbon atoms at a temperature of from about 80° C. to about 240° C. in the presence of an acid catalyst, wherein the catalyst is a blend of at least one perfluorinated polymer containing sulfonic acid groups and at least one perfluorinated polymer diluent.

Preferred monoolefins are C$_2$ to C$_5$ monoolefins, for example, ethylene, propylene, isobutylene, 1-butene, 2-butene, 2-methyl-2-butene, and mixtures thereof. The monoolefin(s) can also be diluted with an inert gas, such as nitrogen. To minimize competing oligomerization of the olefin(s), the reaction is conducted in the presence of an excess of toluene. Typically, the mole ratio of toluene to olefin varies from about 1.5:1 to about 10:1, preferably about 2:1 to about 5:1.

The reaction can be carried out either as a batch or continuous type of operation. When employed as a batch operation, the use of vigorous mechanical stirring or shaking is recommended. When employed as a continuous process, the feedstreams can be contacted with the catalyst in any suitable reactor. The pressure in the reaction zone will depend on the reactor configuration, temperature and olefin reactants, but can be between about 0.01 atm. to about 150 atm. Preferably, the pressure is between about 0.1 atm. and about 75 atm.

Reaction temperatures can be varied between about 80° C. and about 240° C. Although the activity of the catalyst generally increases with increasing temperature, the catalyst may begin to decompose above about 250° C. The preferred reaction temperature is between about 150° C. and about 200° C. The reaction can be run in the gas phase or the liquid phase, depending on the temperature and pressure.

Products of the reaction are generally alkylbenzenes derived from the alkylation of toluene para to the methyl group. Some olefin oligomers are also formed, especially at low ratios of toluene to olefin.

Other acid-catalyzed hydrocarbon conversion reactions such as alkylation of benzene and isoparaffins, isomerization of alkanes, and disproportionation of toluene can also be carried out using catalysts which are blends of perfluorinated ion-exchange resins containing —$SO_3H$ groups and perfluorinated diluent polymers.

However, for all of the acid-catalyzed reactions discussed above, if the reactants, products, and solvent produce a significantly polar reaction mixture, a "leveling effect" of the catalytic activity of the catalyst blend may occur, wherein the activity of the blend becomes the same as that of an acid-equivalent amount of perfluorinated polymer containing —$SO_3H$ groups alone, due to an increase in the activity of the latter. Presumably, this occurs because of swelling of the catalysts. Thus, a reaction mixture that is substantially nonpolar, i.e., largely but not necessarily wholly nonpolar, is desired. Use of the catalyst blend, even in a polar reaction mixture, is advantageous because the catalyst blend is less expensive to use than a perfluorinated sulfonic acid polymer alone. However, to maximize the activity of the catalyst blend, a substantially nonpolar reaction mixture is required. Preferably, the reaction mixture is nonpolar.

To further illustrate the innovative aspects of the present invention, the following examples are provided.

EXAMPLE 1

The perfluorinated ion-exchange polymer containing —$SO_3H$ groups which was used in catalysts A-D was the hydrolyzed form of a melt-fabricable precursor, wherein the precursor is a copolymer of tetrafluoroethylene (TFE) and perfluoro(3,6-dioxa-4-methyl-7-octenesulfonyl fluoride (PSEPVE) having an equivalent weight of about 1100. Catalyst B was a blend of perfluorinated polymer containing —$SO_3H$ groups and a perfluorinated polymer containing —$CO_2H$ groups. The perfluorinated polymer containing —$CO_2H$ groups was the hydrolyzed form of a melt-fabricable precursor, wherein the precursor is a copolymer of tetrafluoroethylene (TFE) and methyl perfluoro-(4,7-dioxa-5-methyl-8-nonenoate) (EVE). Catalyst C was a blend of a perfluorinated polymer containing —$SO_3H$ groups and Teflon ® FEP, a fluorinated ethylene/propylene polymer available from E. I. du Pont de Nemours and Company Catalyst D was a blend of a perfluorinated polymer containing —$SO_3H$ groups and Teflon ®, a poly(tetrafluoroethylene) available from E. I. du Pont de Nemours and Company.

The ion-exchange capacity (IEC) of the polymer blends was determined by titration, using phenolphthalein as indicator. Typically, 1.0-1.5 g of blend polymer was added to 10 mL of distilled water containing 1.0 g of KCl (to displace the protons from the —$SO_3H$ sites) and 5 drops (approximately 0.25 mL) of phenolphthalein (1%) in methanol. The liberated acid was titrated with standardized 0.1 N NaOH. Equilibrium is established slowly and an endpoint was declared only when the pink color of the indicator was persistent for 10 minutes. The IEC measures the total number of titratable acid sites in the polymer per gram of polymer.

The composition of Catalyst B was determined by exchanging the blend with aqueous KCl at about 80° C. for 1 hour. This procedure converted the —$SO_3H$ to —$SO_3K$ (2.32% K by elemental analysis). Another sample of the blend was exchanged with aqueous potassium carbonate at about 80° C. for 1 hour. This procedure converted both acidic (—$SO_3H$ and —$CO_2H$) groups to the potassium form (2.93% K). This corresponds to a 79:21 blend of perfluorinated polymer containing —$SO_3H$ groups:perfluorinated polymer containing —$CO_2H$ groups.

The blend compositions for Catalysts C and D were calculated from the titration-derived IEC values as shown in Equation 1:

$$\% \text{ PFIEP}-SO_3H = \frac{(IEC \text{ of blend})}{(IEC \text{ of } PFIEP-SO_3H)} \times 100$$

with PFIEP=perfluorinated ion-exchange polymer.

A 60 cc quartz version of a Fischer Porter (FP) tube was charged with catalyst (see Table 1), solvent (toluene, 25 mL, 0.236 mol) and internal standard (chlorobenzene, 1.0 g, 0.089 mol). A reactor head assembly was fitted to the FP tube. Isobutylene (15 g, 0.268 mol) was transferred to the tube from an ISCO pump via the reactor head assembly The reactor was heated to 110° C. or 35 minutes and then cooled to room termperature. Capillary gas chromatography with standardized response factors was used for the analysis. The activity in Table 1 is based on the amount of isobutylene reacted, which is calculated from the total amount of dimers, trimers, tetramers and p-(t-butyl)toluene formed.

TABLE 1

| Catalyst | Isobutylene Oligomerization | |
|---|---|---|
| | PFIEP —$SO_3H$[a] | Activity[b] |
| (g) | (%) | (TOR) |
| A (0.25) | 100 | 19 |
| B (0.12) | 79 | 58 |
| C (0.12) | 66 | 68 |
| D (0.12) | 62 | 120 |

[a]Perfluorinated ion-exchange polymer containing —$SO_3H$ groups.
[b]TOR = mmol of product per mequiv of total IEC per minute.

This example shows that catalysts which are blends of a perfluorinated ion-exchange polymer containing —$SO_3H$ groups and an inert perfluorinated diluent are more active as isobutylene oligomerization catalysts than the polymer with —$SO_3H$ groups.

EXAMPLE 2

A 60 cc quartz FP tube was charged with a catalyst selected from catalysts A through D as defined in Example 1, toluene (40 mL, 0.377 mol) and internal standard (chlorobenzene, 1.0 g, 0.0089 mol). A reactor head assembly was fitted to the FP tube. Isobutylene (5 g, 0.089 mol), was transferred to the FP tube from an ISCO pump via the reactor head assembly. The reactor was heated to 150° C. for 60 minutes and then cooled to room temperature. Capillary GC with standardized response factors was used for the analysis. The activity in Table 2 is based on the amount of p-(t-butyl)toluene formed during the reaction. Isobutylene dimers and trimers are also formed.

TABLE 2

| Catalyst (g) | Toluene Alkylation PFIEP —SO$_3$H[a] (%) | Activity[b] (TOR) |
|---|---|---|
| A (0.25) | 100 | 0.8 |
| B (0.25) | 79 | 4.9 |
| C (0.25) | 66 | 4.2 |
| D (0.25) | 62 | 7.3 |

[a] Perfluorinated ion-exchange polymer containing —SO$_3$H groups.
[b] TOR = mmol of product per mequiv of total IEC per minute.

This example shows that catalysts which are blends of a perfluorinated ion-exchange polymer containing —SO$_3$H groups and an inert perfluorinated diluent are more active as toluene alkylation catalysts than the polymer with —SO$_3$H groups itself.

EXAMPLE 3

Catalysts A to D were as defined in Example 1. Catalyst E is a 1:1 blend of a perfluorinated polymer containing —SO$_3$H groups and a perfluorinated polymer containing —CO$_2$H groups. Catalyst F was a film of a perfluorinated polymer containing —CO$_2$H groups. A 60 cc quartz FP tube was charged with catalyst (see Table 3), methanol (9.5 g, 0.297 mol) and internal standard (heptane, 0.5 g, 0.005 mol). A reactor head was fitted to the FP tube and then isobutylene was transferred to the tube via the reactor head assembly. The reactor was heated to 80° C. for 120 minutes and then cooled to room temperature. Capillary gas chromatography with standardized response factors was used for the analysis.

TABLE 3

| Catalyst (g) | MTBE Sythesis PFIEP —SO$_3$H[a] (%) | Activity[b] (TOR) | Mesh |
|---|---|---|---|
| A (0.25) | 100 | 1.0 | 10–35 |
| B (0.25) | 79 | 1.0 | 10–35 |
| C (0.25) | 66 | 0.9 | 10–35 |
| C (0.25) | 66 | 1.1 | 10–35 |
| C (0.25) | 66 | 0.9 | <35 |
| C (0.25) | 66 | 0.8 | <35 |
| D (0.25) | 62 | 1.2 | 10–35 |
| D (0.25) | 62 | 1.0 | 10–35 |
| D (0.25) | 62 | 1.0 | <35 |
| E (0.25) | 50 | 0.8 | 10–35 |
| F (0.25) | 0 | trace | film |

[a] Perfluorinated ion-exchange polymer containing —SO$_3$H groups.
[b] TOR = mmol of product per mequiv of total IEC per minute.

This example shows that in methanol there is not a significant difference in the activity of the diluted and undiluted perfluorinated polymers containing —SO$_3$H groups because methanol is a swelling solvent for perfluorinated ionomers which makes all of the acid sites accessible. The volume expansions for Catalysts A, B, and E are 133, 10 and 53%, respectively. Thus, the nature of the solvent or reaction mixture affects the relative activities of the catalysts. As polarity is increased, the difference in the activity of the diluted and undiluted catalysts decreases.

What is claimed is:

1. An improved process for acid catalyzed hydrocarbon conversion reactions, wherein the improvement comprises use of a catalyst which is a blend of at least one perfluorinated ion-exchange polymer containing sulfonic acid groups and at least one perfluorinated polymer diluent in a substantially nonpolar reaction mixture.

2. The process of claim 1 wherein the polymer diluent is selected from poly(tetrafluoroethylene), copolymers of tetrafluoroethylene and hexafluoropropylene, perfluorinated polymers containing carboxylic acid functional groups, copolymers of tetrafluoroethylene and perfluorinated polymers containing carboxylic acid functional groups, or derivatives thereof.

3. The process of claim 2 wherein the perfluorinated ion-exchange polymer containing sulfonic acid groups is a hydrolyzed copolymer of tetrafluoroethylene and perfluoro(3,6-dioxa-4-methyl-7-octenesulfonyl fluoride).

4. The process of claim 3 wherein a blend of said perfluorinated polymer containing sulfonic acid groups, and a polymer diluent of tetrafluoroethylene is in the ratio of from about 20:1 to about 1:1.

5. The process of claim 4 wherein the ratio is from about 10:1 to about 1:1.

6. The process of claim 3 wherein the polymer diluent is a hydrolyzed copolymer of tetrafluoroethylene and methyl perfluor(4,7-dioxa-5-methyl-8-nonenoate).

7. The process of claim 3 wherein the polymer diluent is poly(tetrafluoroethylene).

8. The process of claim 3 wherein the polymer diluent is a fluorinated ethylene/propylene polymer.

9. The process of claim 1 wherein the reaction is an acid-catalyzed oligomerization of olefins.

10. The process of claim 9 wherein the olefins comprise monoolefins of 2 to 5 carbon atoms or a mixture thereof.

11. The process of claim 10 wherein the oligomerization is conducted at a temperature of from about 80° C. to about 240° C.

12. The process of claim 10 wherein the oligomerization is conducted at a pressure of from about 0.01 atm. to about 150 atm.

13. The process of claim 10 wherein the olefins are diluted with an inert gas.

14. The process of claim 1 wherein the reaction is an acid catalyzed alkylation of toluene with monoolefin.

15. The process of claim 14 wherein monoolefins of 2 to 5 carbon atoms, or a mixture thereof, are contacted with the toluene.

16. The process of claim 15 wherein the olefins are diluted with an inert gas.

17. The process of claim 15 wherein the mole ratio of toluene to olefins is from about 1.5:1 to about 10:1.

18. The process of claim 15 wherein the mole ratio of toluene to olefins is from about 2:1 to about 5:1.

19. The process of claim 15 wherein the alkylation is conducted at a pressure of from about 0.01 atm. to about 150 atm.

20. The process of claim 15 wherein the alkylation is conducted at a temperature of from about 80° C. to about 240° C.

21. A method of catalysis comprising use of a blend of at least one perfluorinated ion-exchange polymer containing sulfonic acid groups and at least one perfluorinated polymer diluent in a substantially nonpolar reaction mixture.

* * * * *